(12) United States Patent
Jagga et al.

(10) Patent No.: US 10,828,104 B2
(45) Date of Patent: Nov. 10, 2020

(54) SURGICAL NAVIGATION SYSTEM USING IMAGE SEGMENTATION

(71) Applicants: Arun Victor Jagga, Toronto (CA); Cameron Piron, Toronto (CA)

(72) Inventors: Arun Victor Jagga, Toronto (CA); Cameron Piron, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 571 days.

(21) Appl. No.: 15/510,572

(22) PCT Filed: Sep. 15, 2014

(86) PCT No.: PCT/CA2014/050872
§ 371 (c)(1),
(2) Date: Mar. 10, 2017

(87) PCT Pub. No.: WO2016/041050
PCT Pub. Date: Mar. 24, 2016

(65) Prior Publication Data
US 2017/0196641 A1    Jul. 13, 2017

(51) Int. Cl.
*A61B 34/20*  (2016.01)
*A61B 34/00*  (2016.01)
(Continued)

(52) U.S. Cl.
CPC ............. *A61B 34/00* (2016.02); *A61B 34/20* (2016.02); *A61B 90/10* (2016.02); *A61B 90/39* (2016.02);
(Continued)

(58) Field of Classification Search
CPC . A61B 34/20; A61B 2034/2055; A61B 34/30; A61B 34/25; A61B 2034/2057; A61B 90/37; A61B 2034/2072; A61B 2090/365; A61B 2034/102; A61B 2090/3983; A61B 2090/371;
(Continued)

(56) References Cited

U.S. PATENT DOCUMENTS 5,957,934 A * 9/1999 Rapoport ............... A61B 90/11
600/417
8,073,528 B2 * 12/2011 Zhao ..................... B25J 9/1689
600/424
(Continued)

FOREIGN PATENT DOCUMENTS

WO    WO2012/131610 A1    10/2012

*Primary Examiner* — Allen Porter
*Assistant Examiner* — Adreanne A. Arnold
(74) *Attorney, Agent, or Firm* — Ridout & Maybee LLP

(57) ABSTRACT

A system for tracking a piece of medical equipment intra-operatively using a collinear array of fiducial markers positioned at known fixed distances relative to each other on the medical equipment and a camera capturing an image on a single image plane. Representations of the fiducial markers are segmented from a captured image, 3D orientation and position of the medical equipment are calculated using the segmented representations, and the orientation and position of the medical equipment are tracked relative to the camera. The orientation and position of the medical equipment may be registered within a 3D virtual space. The system may be used as part of a surgical navigation system.

20 Claims, 16 Drawing Sheets

(51) Int. Cl.
*A61B 90/10* (2016.01)
*A61B 90/00* (2016.01)

(52) U.S. Cl.
CPC .............. *A61B 2034/2055* (2016.02); *A61B 2034/2057* (2016.02); *A61B 2090/3983* (2016.02)

(58) Field of Classification Search
CPC ...... A61B 2090/3945; A61B 2034/301; A61B 2034/2046; A61B 90/30
See application file for complete search history.

(56) References Cited

U.S. PATENT DOCUMENTS

| | | | |
|---|---|---|---|
| 2005/0124988 A1* | 6/2005 | Terrill-Grisoni | A61B 17/3403 606/53 |
| 2006/0235290 A1* | 10/2006 | Gabriel | A61B 17/157 600/407 |
| 2009/0088897 A1* | 4/2009 | Zhao | G06K 9/3216 700/250 |
| 2010/0168763 A1* | 7/2010 | Zhao | A61B 34/30 606/130 |
| 2011/0015521 A1* | 1/2011 | Faul | A61N 5/1049 600/426 |
| 2012/0020547 A1 | 1/2012 | Zhao et al. | |
| 2012/0209288 A1* | 8/2012 | Robinson | A61B 34/30 606/130 |
| 2014/0107471 A1 | 4/2014 | Haider et al. | |
| 2016/0187481 A1* | 6/2016 | Zalev | G01S 15/06 367/7 |
| 2019/0254757 A1* | 8/2019 | Piron | A61B 5/7405 |

\* cited by examiner

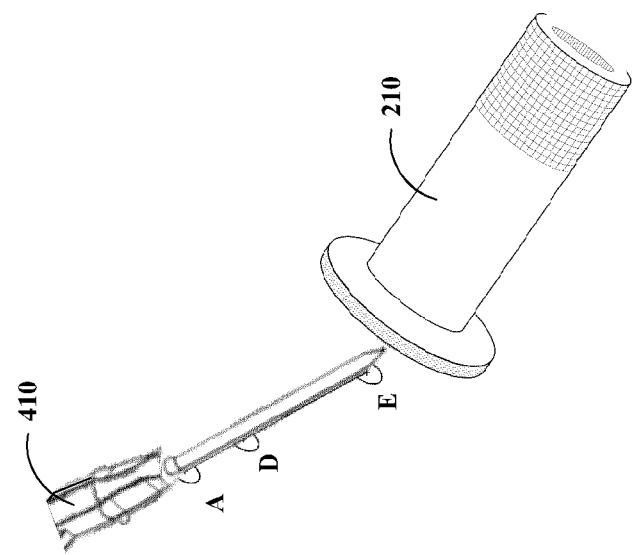
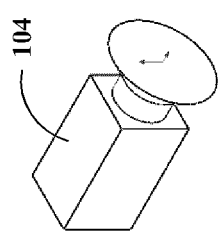
Figure 5

| LED # | Combination 1 | Combination 2 | Combination 3 |
|---|---|---|---|
| 1500A | A | F | K |
| 1500B | B | G | L |
| 1500C | C | H | M |
| 1500D | D | I | N |
| 1500E | E | J | O |

SURGICAL NAVIGATION SYSTEM USING IMAGE SEGMENTATION

FIELD

The present disclosure is generally related to image guided medical procedures using a surgical instrument, such as a catheter, a biopsy needle, a fiber optic scope, an optical coherence tomography (OCT) probe, a micro ultrasound transducer, an electronic sensor or stimulator, or an access port based surgery.

BACKGROUND

In the example of a port-based surgery, a surgeon or robotic surgical system may perform a surgical procedure involving tumor resection, for example, in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

FIG. 1A illustrates the insertion of an access port into a human brain, for providing access to internal brain tissue during a medical procedure. In FIG. 1A, access port 12 is inserted into a human brain 10, providing access to internal brain tissue. Access port 12 may include such instruments as catheters, surgical probes, or cylindrical ports such as the NICO BrainPath™. Surgical tools and instruments may then be inserted within the lumen of the access port in order to perform surgical, diagnostic or therapeutic procedures, such as resecting tumors as necessary. The present disclosure may apply equally well to catheters, DBS needles, a biopsy procedure, and also to biopsies and/or catheters in other medical procedures performed on other parts of the body, for example.

In the example of a port-based surgery, a straight or linear access port 12 is typically guided down a sulci path of the brain. Surgical instruments would then be inserted down the access port 12. Once the surgical instrument is inserted, there is typically a desire to visualize and determine the depth of penetration of the surgical instrument down the access port intraoperatively. It would be useful to provide mechanisms to indicate depth penetration on surgical instruments surgical instruments when performing medical procedures.

Further, space in the surgical operating theater is typically a commodity. Therefore, reducing the footprint of required equipment without jeopardizing effectiveness of the procedure may help to improve surgical procedures.

SUMMARY

The present disclosure is generally related to image guided medical procedures using an access port. This port-based surgery approach may allow a surgeon, or robotic surgical system, to perform a surgical procedure involving tumor resection, for example, in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

In various examples, the present disclosure describes methods and apparatuses that allow a linear section of a medical equipment such as a medical instrument, in particular a surgical instrument, to be tracked by a monocular imaging sensor (e.g., video camera, surgical scope, or wide field scope) of a surgical system, using an attached linear array of active fiducial markers, during a surgical procedure. The present disclosure may be implemented as part of a navigation system, which may include additional 3D tracking components.

Although the present disclosure makes reference to a monocular imaging sensor or a monocular camera, any camera that captures an image on a single image plane may take the role of the monocular camera. For example, a binocular camera operating in single lens mode may function as a monocular camera.

In some examples, the present disclosure provides a system for tracking a piece of medical equipment intraoperatively within a three-dimensional virtual space, the system may include: a collinear array of fiducial markers positioned at known fixed distances relative to each other on the medical equipment; a camera for capturing an image of the medical equipment on a single image plane, the captured image including at least some of the fiducial markers; and a processor receiving input from the camera, the processor executing instructions to track the medical equipment by: segmenting representations of the fiducial markers from the captured image; calculating three-dimensional orientation and position of the medical equipment using the segmented representations; tracking the three-dimensional orientation and position of the medical equipment relative to the camera; and registering the calculated three-dimensional orientation and position of the medical equipment within the three-dimensional virtual space.

In some examples, the present disclosure provides a surgical navigation system for tracking medical equipment intraoperatively, the system may include: a first medical equipment; a collinear array of a first set of fiducial markers positioned at known fixed distances relative to each other on the first medical equipment; a first camera for capturing an image of the first medical equipment on a single image plane, the captured image including at least some of the first set of fiducial markers; a second camera for tracking a second set of fiducial markers; and a processor receiving input from the first camera and the second camera, the processor executing instructions to: register the second set of fiducial markers within a three-dimensional virtual space; segment representations of the first set of fiducial markers from the captured image; calculate three-dimensional orientation and position of the surgical instrument using the segmented representations; and register the three-dimensional orientation and position of the first medical equipment within the three-dimensional virtual space.

The present disclosure may be used with any compatible surgical navigation system. A non-limiting example of such a surgical navigation system is outlined in the PCT application no. PCT/CA2014/050270 entitled "SYSTEMS AND METHODS FOR NAVIGATION AND SIMULATION OF INVASIVE THERAPY", which claims the priority benefit of U.S. Provisional Patent Application Ser. Nos. 61/800,155 and 61/924,993, the entireties of which are all incorporated herein by reference. The disclosure of PCT Application No. PCT/CA2014/050266, titled "SYSTEM AND METHOD FOR DYNAMIC VALIDATION, CORRECTION OF REGISTRATION FOR SURGICAL NAVIGATION" and filed on Mar. 14, 2014, is also incorporated herein by reference in its entirety.

BRIEF DESCRIPTION OF THE DRAWINGS

Embodiments will now be described, by way of example only, with reference to the drawings, in which:

FIG. 5 illustrates an example surgical setup for a minimally invasive surgery when employing an access port and an example instrument mounted with a linear array of active fiducial markers;

DETAILED DESCRIPTION

Figure 1A:
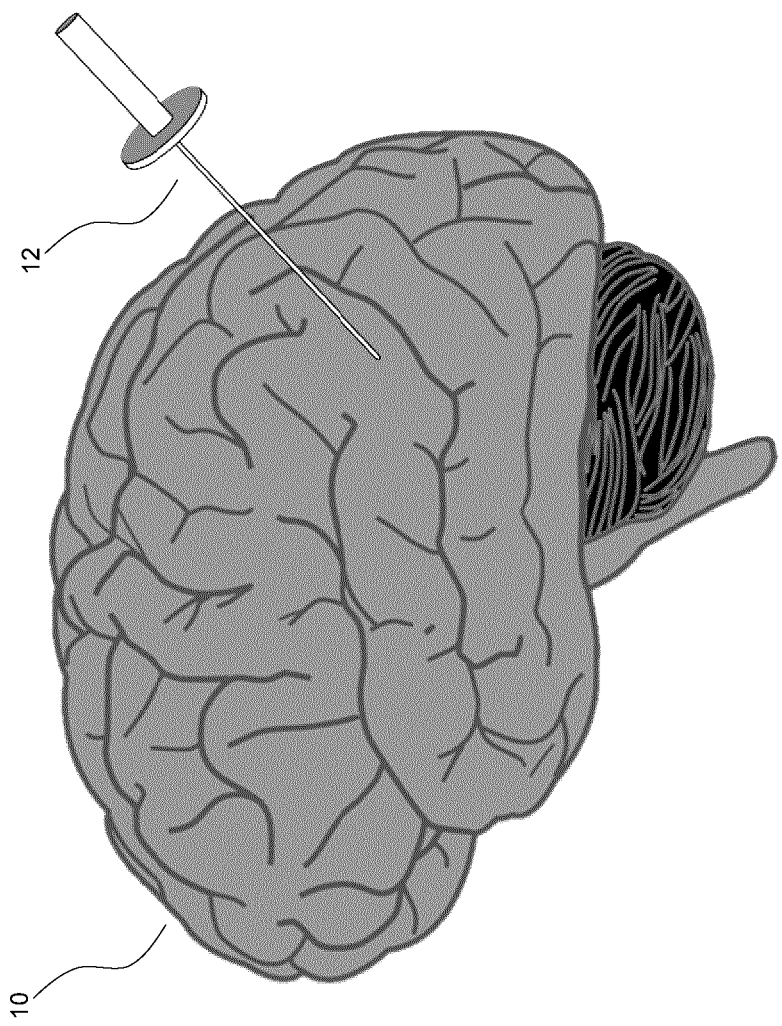
FIG. 1A illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It will be understood by those of ordinary skill in the art that the embodiments described herein may be practiced without these specific details. Also, the description is not to be considered as limiting the scope of the claims appended hereto.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Various apparatuses or processes will be described below to provide examples of embodiments of the invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses or processes described below. It is possible that an apparatus or process described below is not an embodiment of any claimed invention.

Furthermore, in the following passages, different aspects of the embodiments are defined in more detail. In particular, any feature described with respect to one embodiment, such as an embodiment indicated as being preferred or advantageous, may be combined with at least one other feature or features described with respect to another embodiment, such as another embodiment indicated as being preferred or advantageous.

Some embodiments of the present disclosure provide overlays of medical equipment for assisting a surgeon in visualizing a surgical area or object of interest, such as a piece of medical equipment (e.g., a medical instrument), and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

An example of an access port is an intracranial conduit which may be employed in neurological procedures in order to provide access to internal tissue pathologies, such as tumors. One example of an intracranial access port is the BrainPath™ surgical access port provided by NICO, which may be inserted into the brain via an obturator with an atraumatic tip. Such an access port may be employed during a surgical procedure, by inserting the access port, via the obturator that is received within the access port, through the white and gray of the brain to access a surgical site.

Minimally invasive brain surgery using access ports is a method of performing surgery on the brain, such as for treatment of brain tumors. In some examples, the present disclosure provides systems and methods that may assist in minimally invasive brain surgery.

Figure 1B:
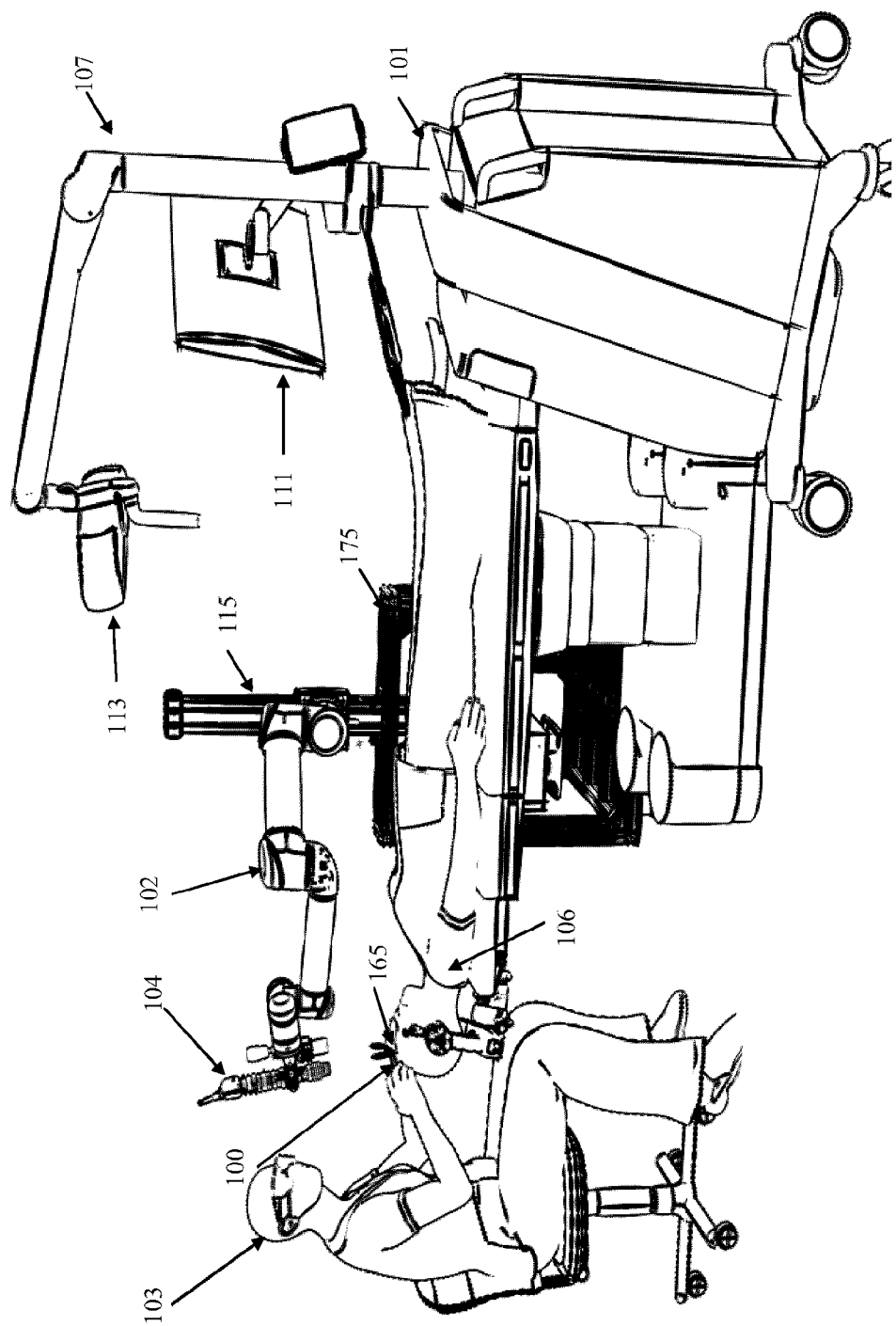
FIG. 1B illustrates a minimally invasive surgical procedure employing a surgical system.

To address intracranial surgical concerns, specific products such as the NICO BrainPath™ port have been developed for port-based surgery. FIG. 1B is a diagram illustrating components of an exemplary surgical system used in such a port-based surgery. FIG. 1B shows a navigation system 107 including an equipment tower 101, optical tracking system 113, display 111, an intelligent positioning system 175 and tracking markers 165 used to track surgical instruments or access port 100. Tracking system 113 may also be considered an optical tracking device which tracks the tracking markers 165. Although FIG. 1B shows a navigation system 107 as part of the surgical system, in some examples the surgical system may not include any navigation system. Instead, viewing and limited tracking of the port-based surgery may be carried out using an external scope 104. The external scope 104 may be a video camera that captures images in a single image plane. The external scope 104 may typically be a single lens camera, or in some examples may be a dual-lens camera operating in single lens mode.

As shown in FIG. 1B, surgeon 103 is resecting a tumor in the brain of a patient 106, through port 100. External scope 104, attached to automated arm 102, is typically used by the surgeon to enhance visibility of the brain at the distal end of the port 100. The external scope 104 may be zoomed-in or zoomed-out, and its output may be depicted on a visual display that may contain surgical equipment in the field of view of the external scope 104.

The described corridors normally have very small openings for tools or other medical equipment. The surgeons' visibility of the surgical operating area is therefore limited due to the small corridors and areas the operations take place in. To enhance visibility of the surgical area of interest, the external scope 104 (e.g., a standoff video scope or microscope) which images the surgical site of interest at a greater magnification and depicts it on a heads up display or microscope viewing lenses, may be used so the surgeon 103 can clearly view the site.

A typically feature of surgical navigation systems 107 employed during navigated surgical procedures is the ability to track medical instruments. These systems typically perform tracking through the use of active or passive fiducial markers mounted on the instrument(s) being tracked in combination with a detector device used to locate said fiducial markers. Examples of a navigation system include the passive Polaris™ System provided by NDI. Generally, active fiducial markers are those that generate their own signal (e.g., a light signal such as an infrared light), which may be detected by the detector device. Active fiducial markers may be individually powered or may draw power from one or more shared power sources. Generally, passive fiducial markers (also referred to as inactive fiducial markers) are those that do not generate their own signal, but are nonetheless detectable by the detector device. For example, passive fiducial markers may be reflective or otherwise optically distinguishable from their surrounding environment.

Placement of fiducial markers (also referred to as fiducials) on surgical instruments used in these navigation systems are typically restricted to a minimum of three fiducials oriented to form a plane. This restriction can be problematic as it requires the fiducials to take up a greater footprint on the instrument then if the markers were oriented in a collinear manner. This is especially apparent when the fiducials need be a minimum distance apart for effective segmentation by the detector which is the case when employing the Polaris™ system mentioned above. These requirements can result in the addition of bulky and sizeable assemblies to typically used instruments such as a pointer tool, used during navigated surgery to verify instrument positioning. An exemplary assembly 200 having fiducials in a non-collinear arrangement is shown attached to pointer tool 205 in FIG. 2.

Figure 2:
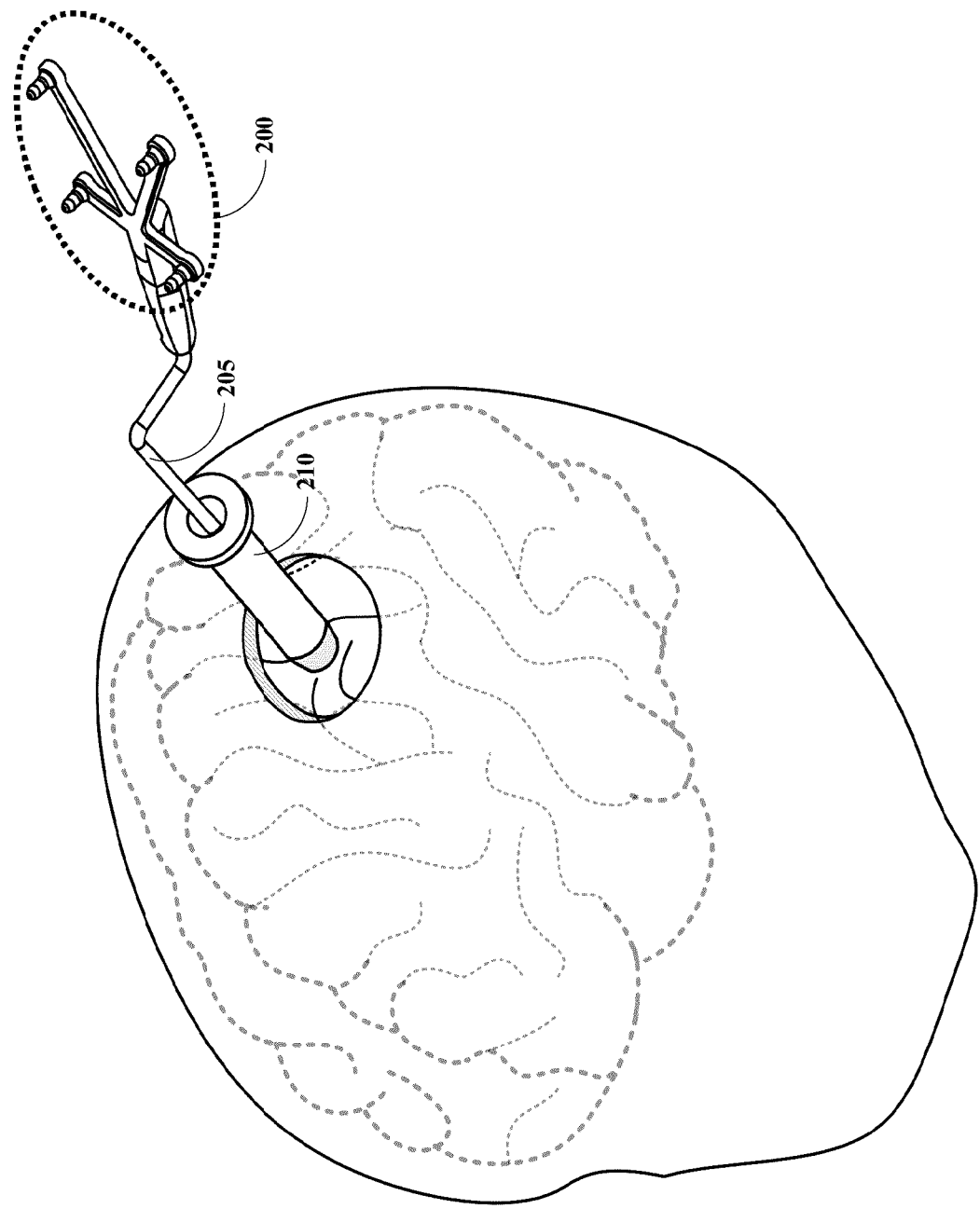
FIG. 2 illustrates a surgical instrument operating within an access port in a patient.

When performing minimally invasive surgical procedures, medical instruments are typically oriented and maneuvered within the small corridor that provides access to the surgical area of interest. An exemplary minimally invasive surgical procedure employing such a corridor is a port based brain tumor resection as depicted in FIG. 2 in which an access port 210, such as the Nico BrainPath™ with a 13 mm diameter opening, is used to access a subcortical tumor. It is apparent from the size of the opening used in this type of surgery that a bulky assembly, such as the assembly 200 provided on the pointer tool 205, may potentially restrict the range of movement of a medical instrument being maneuvered within the corridor. In addition, a bulky assembly may significantly increase the weight of the instrument being maneuvered, which can reduce the dexterity of a surgeon, potentially resulting in increased trauma to the patient.

The planar orientation of the fiducials, both active and passive, when oriented in various angles relative to the detector device may also result in failure or error in dynamic tracking of the instrument.

Figure 3:
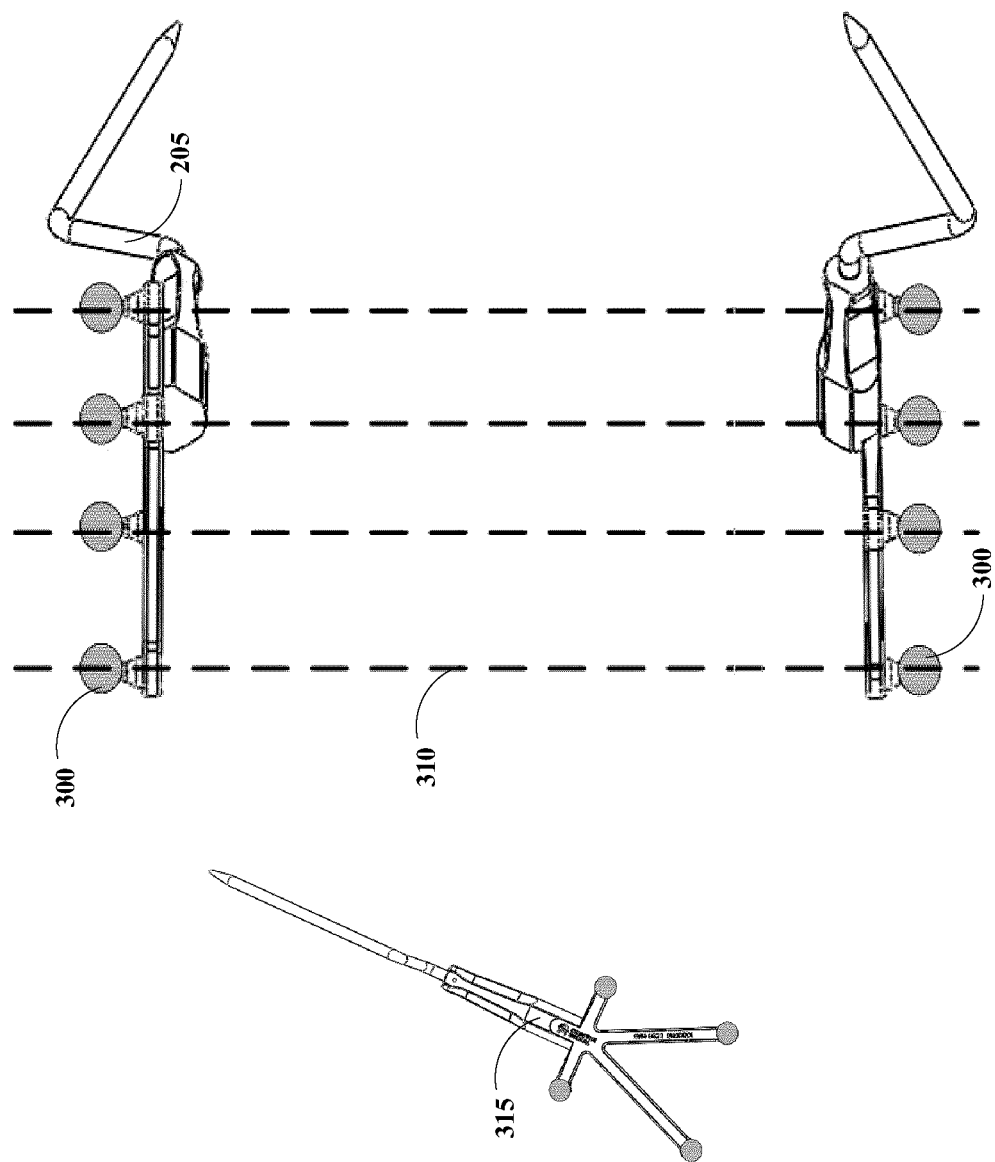
FIG. 3 illustrates an ambiguous view of an optically tracked surgical instrument.

Such failure or error may occur when the plane in which the fiducials lie becomes oriented perpendicular with respect to the imaging plane of the detector. This may be especially apparent in systems employing a monocular detector (e.g., a single lens surgical scope), as an ambiguity may be created in which the direction of the tool could potentially be facing in two directions (towards or away from the detector). An example of such an ambiguity is depicted in FIG. 3 where a monocular camera view is depicted showing two tool orientations in which the fiducials 300 would appear to be identically placed, in the view of the monocular detector, and therefore not differentiable. It is apparent that both the bottom and top orientations of the pointer tool could be valid when the fiducials 300 are detected in an image plane perpendicular to the plane of the fiducials 300. Lines 310 and diagram 315 illustrate the equivalence in positioning of the depicted fiducials and a top view of the pointer tool, respectively, for clarity.

Figure 4:
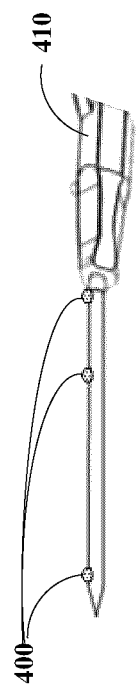
FIG. 4 illustrates an example surgical instrument mounted with a linear array of active fiducial markers.

FIG. 4 illustrates a surgical instrument mounted with a linear array of active fiducials. In a surgical instrument such as a surgical pointer instrument 410, for example, a linear array of fiducials 400 may be aligned along the longitudinal axis of the tool 410. Arranging the fiducials 400 along the longitudinal axis of the tool 410 may help to reduce the overall profile and footprint of the tool 410.

Figure 6:
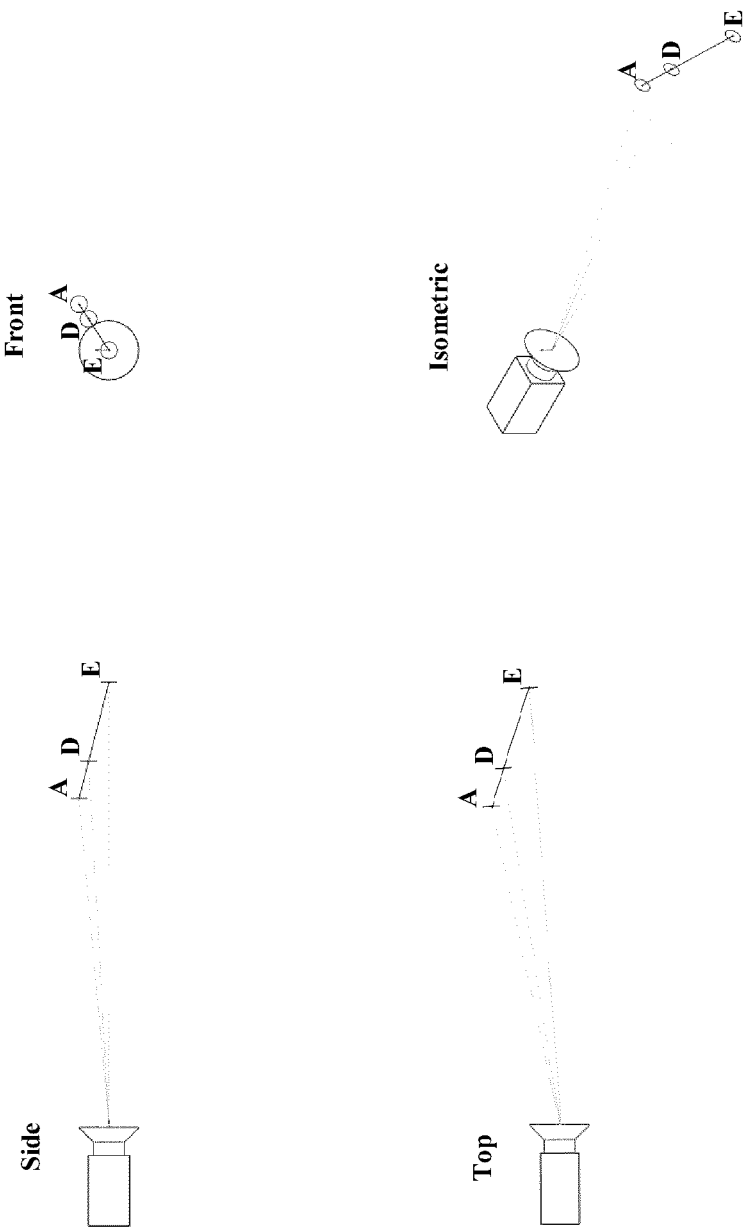
FIG. 6 illustrates multiple views of an example surgical setup for a minimally invasive surgery when employing an access port and an example instrument mounted with a linear array of active fiducial markers.

FIG. 5 depicts a typical surgical operating scenario in which surgical scope 104 (e.g., a surgical single lens camera) is viewing the surgical pointer instrument 410 in a direction approximating the axial direction of the port 210, within which the instrument 410 will be operating. The fiducials located on the surgical pointer instrument 410 in this example embodiment may be active fiducial markers, such as flashing LED emitters each having a different frequency so as to allow the surgical scope 104 (which may be capturing images in a single image plane) to differentiate between them. The LEDs have been labeled as A, D, and E, so as to allow them to be easily identifiable. LED A corresponds to the most proximal LED on the pointer instrument 410, LED D corresponds to the middle LED, and LED E corresponds to the most distal LED. FIG. 6 depicts various views of the camera and LEDs on the instrument being detected, where each view shows a different angle of the physical scenario, to clearly depict the exemplary scenario, including the lines of sight from the detector (in this example, the surgical scope 104) to each fiducial.

Figure 7:
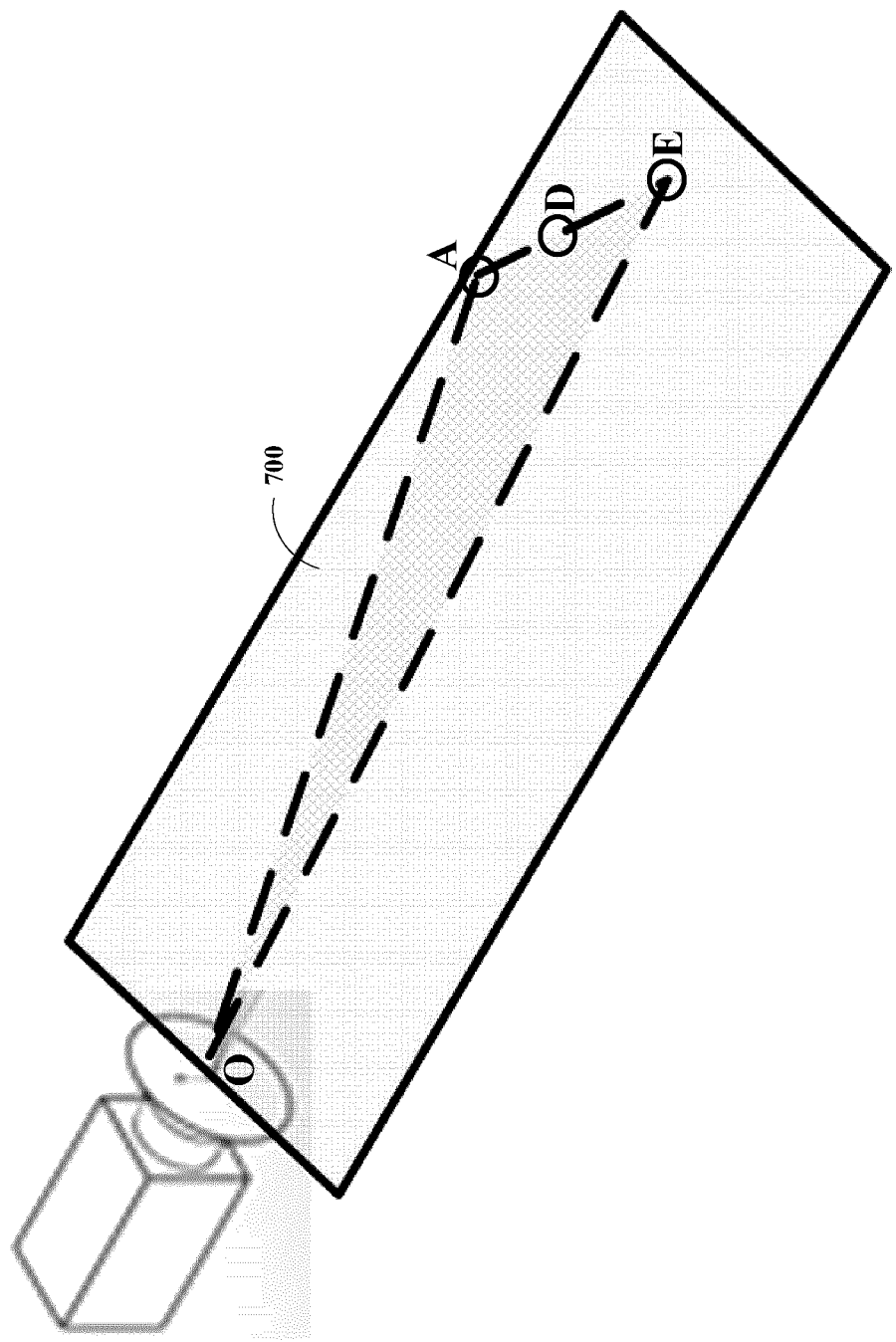
FIG. 7 illustrates an example defined plane with respect to a surgical scope.

It will be assumed moving forward that this scenario can be modeled using the pinhole camera model. This model may serve to adjust for the effects of perspective on detected images. It assumes that all points entering a camera from the physical world come through a pinhole located at the center of the cameras detector plane (referred to as the origin and denoted O, as shown in FIG. 7) and are projected onto an image plane where the image is captured. In order to simplify this problem it may be assumed that the model is a 2D pinhole camera model as opposed to a 3D model. This assumption is justified because the image being captured is that of a linear fiducial array, so all the points of interest lie along a line; adding a point at the origin O will define a plane. This plane is defined to be coincident with the linear fiducial array and the origin point O, located at the center of the sensor of the surgical scope 104. FIG. 7 illustrates this simplification by depicting the plane 700 passing through the linear fiducial array ADE mounted on the pointer instrument 410 and the origin O of the surgical scope's 104 sensor.

Figure 8:
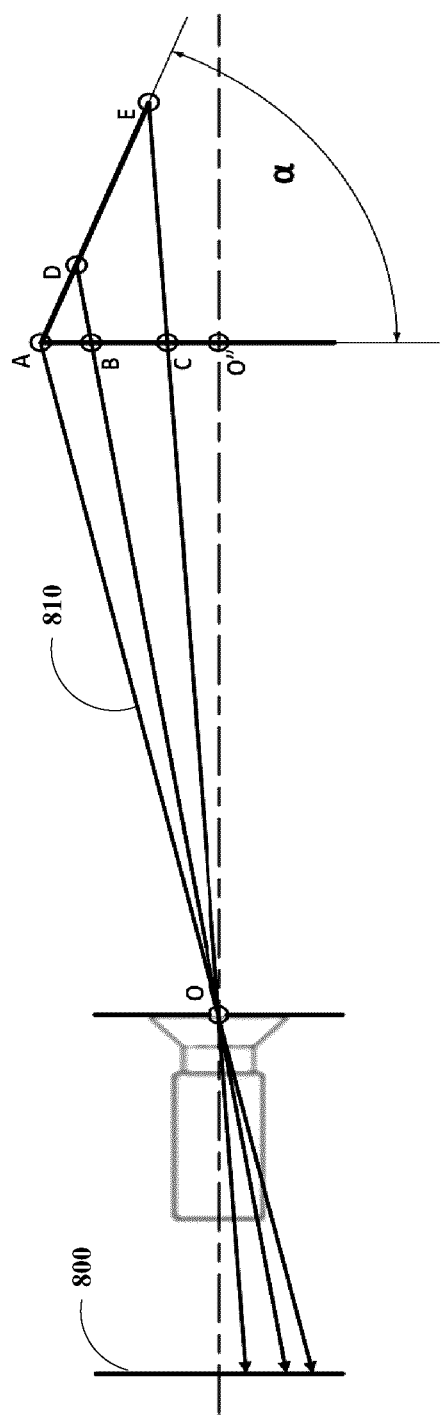
FIG. 8 illustrates an example 2D pinhole camera model setup.

FIG. 8 depicts the 2D pinhole camera model in which the projection lines 810 (i.e., lines from a projection point to the image plane equivalent point) from the points A, D, and E corresponding to the fiducials are shown projecting through the Origin O and onto the image plane 800. The distance of the linear fiducial array from the Origin O and angle of rotation from 0-90°, 0° being when the linear fiducial array is parallel to the image plane and 90° being when the linear fiducial array is perpendicular to the image plane, may be determined as follows. An axis of detection, or the central axis, of the detector (i.e., the pinhole camera) is defined as an axis normal to the image plane 800 and passing through the origin O.

The linear array of uniquely identifiable fiducials can be split into groups where any unique group of two fiducials can be used to define a line segment. These line segments may be captured by the imaging device (e.g., the surgical scope 104) and depending on their position and orientation with respect to the imaging device's sensor will vary in length on the captured image resulting from various phenomena as described as follows.

Figure 9:
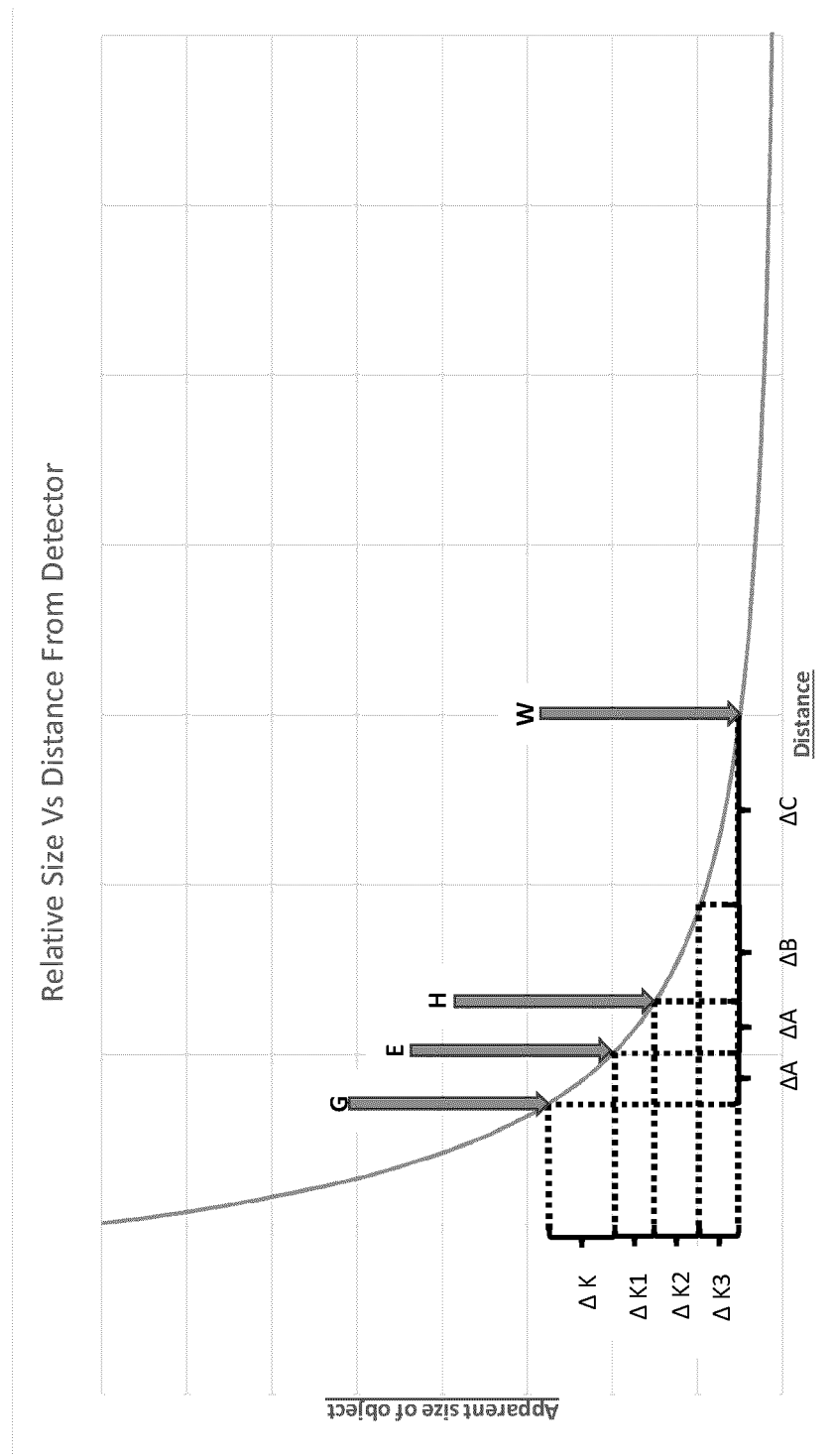
FIG. 9 illustrates a mathematical relationship between the distance of an object and its apparent size.

The first phenomenon that may cause the perceived length of the line segments to change is perspective. A property of line segments when in the field of view of a detector resulting from this phenomenon is that the further they are the smaller their lengths will appear. The decrease in their perspective-dependent apparent lengths will occur at an exponentially inversely proportional rate to their distance from the detector. FIG. 9 depicts a typical correlation of the apparent size of an object (such as a line segment) with respect to its distance from a detector. If a line segment remains substantially perpendicular to the axis of detection (i.e., the line-of-sight) of the detector, as the distance between the line segment and the detector is increased the line segment will decrease in apparent size in an inverse exponential manner. For example, moving from points G to E in FIG. 9, the line segment will change in apparent size by the factor $\Delta K$. This effect is also depicted in the left frame of FIG. 10, where again as the line is moved from distance G to E we see the apparent size of the object located on the image plane 800 changes from 40 to 27.07. The inverse exponential relationship between the distance of an imaged object and its apparent size can also be inferred from this figure by comparing the change in apparent size of the line segment as it is moved a first time from the distance G to E and the change in its apparent size as it is moved a second time from distance E to H. As is shown in the left frame of FIG. 10, the first move (from G to E) causes a change in apparent size of approximately 13 units (shown as $\Delta K$ in FIG. 9) while the second move (from E to H) causes a change in size of about 7 units (shown as $\Delta K1$ in FIG. 9).

The second phenomenon that may cause the perceived length of the line segment to change is the angle of rotation of the linear array of fiducials. If the line segment is moved into a position in which it is not substantially perpendicular to the axis of detection of the detector (i.e., the line segment is rotated or angled with respect to the axis of detection of the detector) its apparent size changes in an inconstant manner over its length. Specifically, each infinitesimally small segment will change in apparent size by differing factors depending on the distance of each infinitesimally small segment from the detector. For example, referring to FIG. 9 and the center frame of FIG. 10, if one end of a line segment was located at distance G from the detector and the other end located at distance W from the detector. Then an approximation of the line segments apparent size could be made by splitting the line segment into three sections—$\Delta A$, $\Delta B$, and $\Delta C$ (as opposed to an infinitesimal number of sections that would yield its actual distance dependent apparent size) as shown in FIG. 9—and applying each reduction factor to each of the sections. The reduction in apparent size when one end of the line segment is located at distance G and the other end at distance W can also be seen in the central frame of FIG. 10 where the 0° angle length is 40 units and the $\alpha°$ angle length is 29.74 units. It should be noted that since one end of the line segment is further from the detector than the other, the line segment is substantially not perpendicular to the axis of detection of the detector and has an angle of rotation (shown as $\alpha$ in FIG. 10) with respect to the axis of detection of the detector. The angling of the line segment will cause a change in the apparent size of the line segment which is independent of its distance from the detector and can be determined using trigonometry as described below. This angle-dependent change in apparent size results from the fact that a component of the line segment shifts into the axial direction 1000 of the imaging detector from the perpendicular direction defined by the image plane 800.

Figure 10:
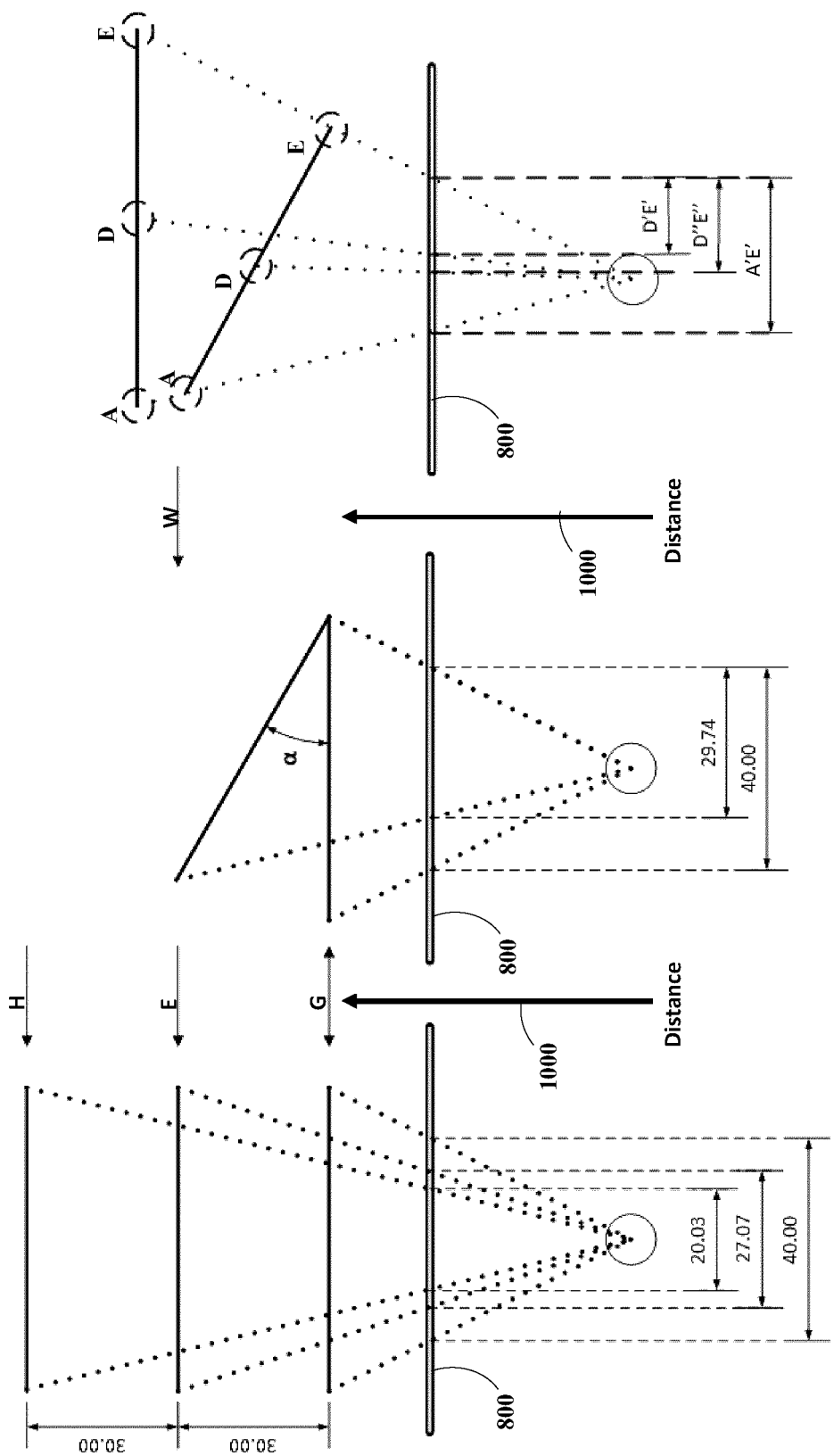
FIG. 10 illustrates example diagrams of the projection of various line segments onto a plane.

It should be noted that although in FIG. 10 the image plane 800 is located in front of the perspective point of the detector as opposed to behind the perspective point of the detector, as is generally done when using the pinhole camera model, the same projections onto the image plane 800 would result if the image plane was located behind the projector at an equivalent distance to the image plane 800 as can be derived from the principle of similar triangles.

It is discernible from the right frame in FIG. 10 that determining the angle and distance of a linear fiducial array from a monocular imaging detector using only two points leads to an under defined problem wherein an ambiguity exists, preventing the attainment of a unique solution. The right frame of FIG. 10 illustrates such an ambiguity wherein fiducials A and E located on the same array in two separate orientations project the same line segment A'E' when detected on the imaging plane 800 of the detector. Therefore, the orientation of the array of linear fiducials occupies cannot be uniquely determined. However, this problem may be alleviated by taking into consideration at minimum a third fiducial (in this example, fiducial D) located anywhere on the fiducial array excluding the locations of the first two fiducials. Using this third fiducial, the fiducials can be split into at minimum two unique groups wherein each group contains two fiducials uniquely defining a line segment. The length of these line segments can then be divided to acquire a ratio of their lengths. These ratios will be unique depending on the distance from the detector and the angle at which the line segment is rotated, preventing any ambiguities from occurring. FIG. 10 illustrates this concept whereby taking the fiducials D and E and their projected line segments D"E" and D'E' on the image plane 800, and dividing them by the line segment projection of A'E' results in two unique ratio values $$\left(\text{i.e. } \frac{D''E''}{A'E'} \neq \frac{D'E'}{A'E'}\right)$$

wherein each value corresponds to a different distance and angle of rotation from the monocular imaging detector.

Figure 11:
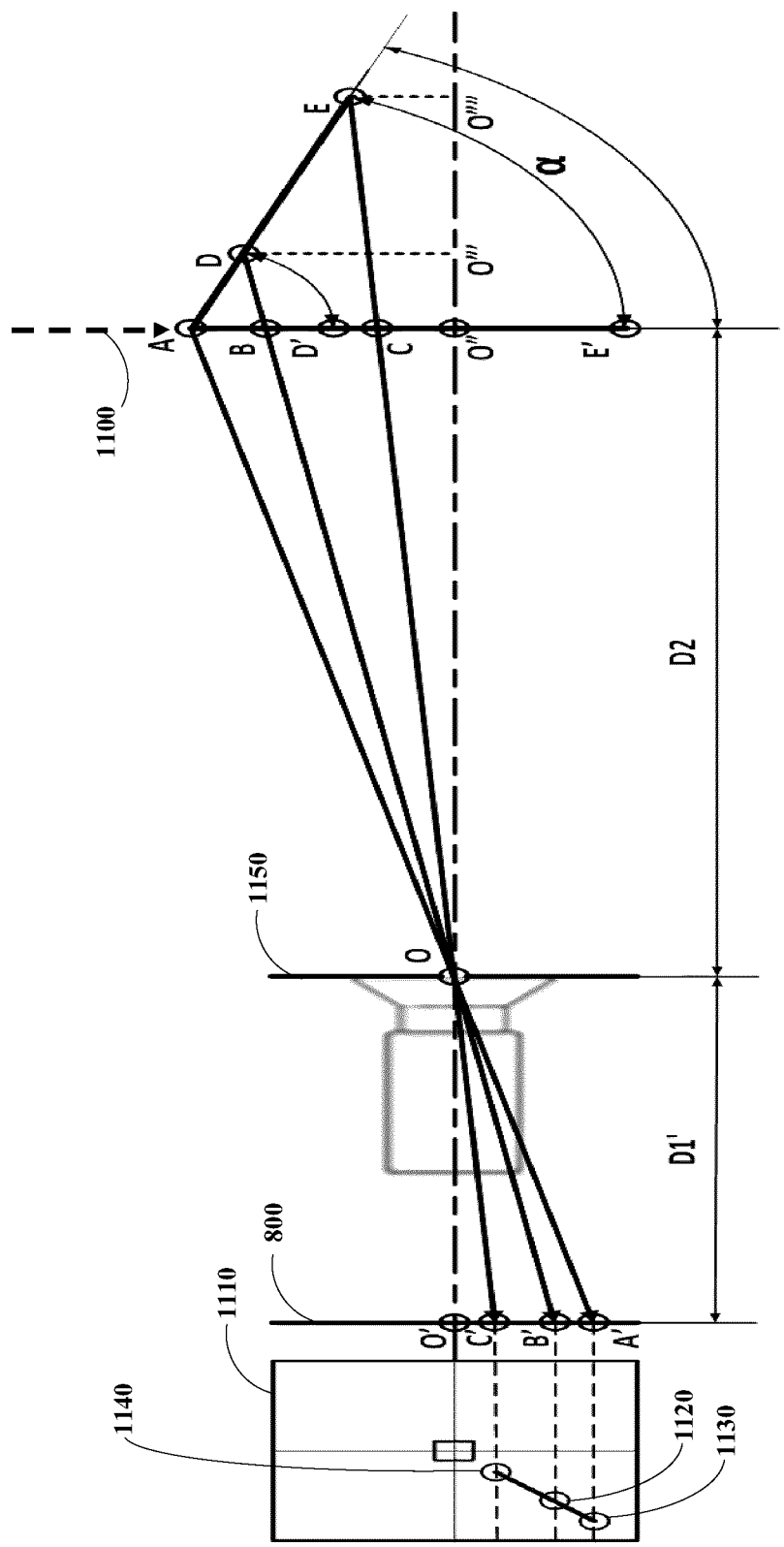
FIG. 11 illustrates an example 2D pinhole camera model.

FIG. 11 depicts the 2D pinhole camera model scenario described above. In this figure the linear fiducial array ADE is rotated to the angle $\alpha°$ from its 0° position represented by line AD'E' at a distance D2 from the principle point O (center point of the image plane (also referred to as the image center) of the imaging detector sensor 1150).

Projection lines AA', DB', and EC' depict the point projections of each of the fiducials A, D, E as they are captured by the camera through the principle point O of the detector on the imaging plane 800. The projected points of the fiducials on the image plane are denoted as follows A' for A, B' for D, and C' for E. To remain consistent, the distance D2 will be taken from one of the two end fiducials located on the linear array of fiducials, in this case the uniquely differentiable fiducial A has been chosen. The distance of the center point O of the detector to the image plane 800 is known and termed the focal length, and denoted D1'. From this diagram the following equalities can be derived:

$$\angle BOO'' = \angle DOO''' = \angle B'OO' \quad (1)$$

$$\angle COO'' = \angle EOO'''' = \angle C'OO' \quad (2)$$

$$\frac{BC*D1'}{D2} = B'C' \quad (3)$$

$$\frac{AB*D1'}{D2} = A'B' \quad (4)$$

$$\frac{B'C'}{A'B'} = \frac{\frac{BC*D1'}{D2}}{\frac{AB*D1'}{D2}} = \frac{BC}{AB} \quad (5)$$

The results of (5) implicate that the measured lengths between pairs of points (forming line segments) as captured by the camera may be used to ratio the points as projected onto a plane represented by the arrow 1100 parallel to the imaging plane but located at the distance D2 from the principle point O of the camera. In this example embodiment, the plane 1100 is defined as being at 0° relative to the rotated angle of the linear array of fiducials ADE. Diagram 1110 represents the actual image being captured by the camera at the image plane 800, where the fiducials A, D, and E are captured in the image as 1130, 1120, and 1110 respectively. The captured image can then be analyzed to compute the lengths of line segments A'B', B'C', or any other line segments as required to produce a relevant ratio value. Using the equalities as described by (1), (2), and (5) derived from the 2D pinhole camera model, a relationship may be derived between the linear array of fiducials ADE angle of rotation $\alpha$ and distance D2 and the ratio of its line segments as captured by the imaging detector $$\frac{B'C'}{A'B'}.$$

Figure 12:
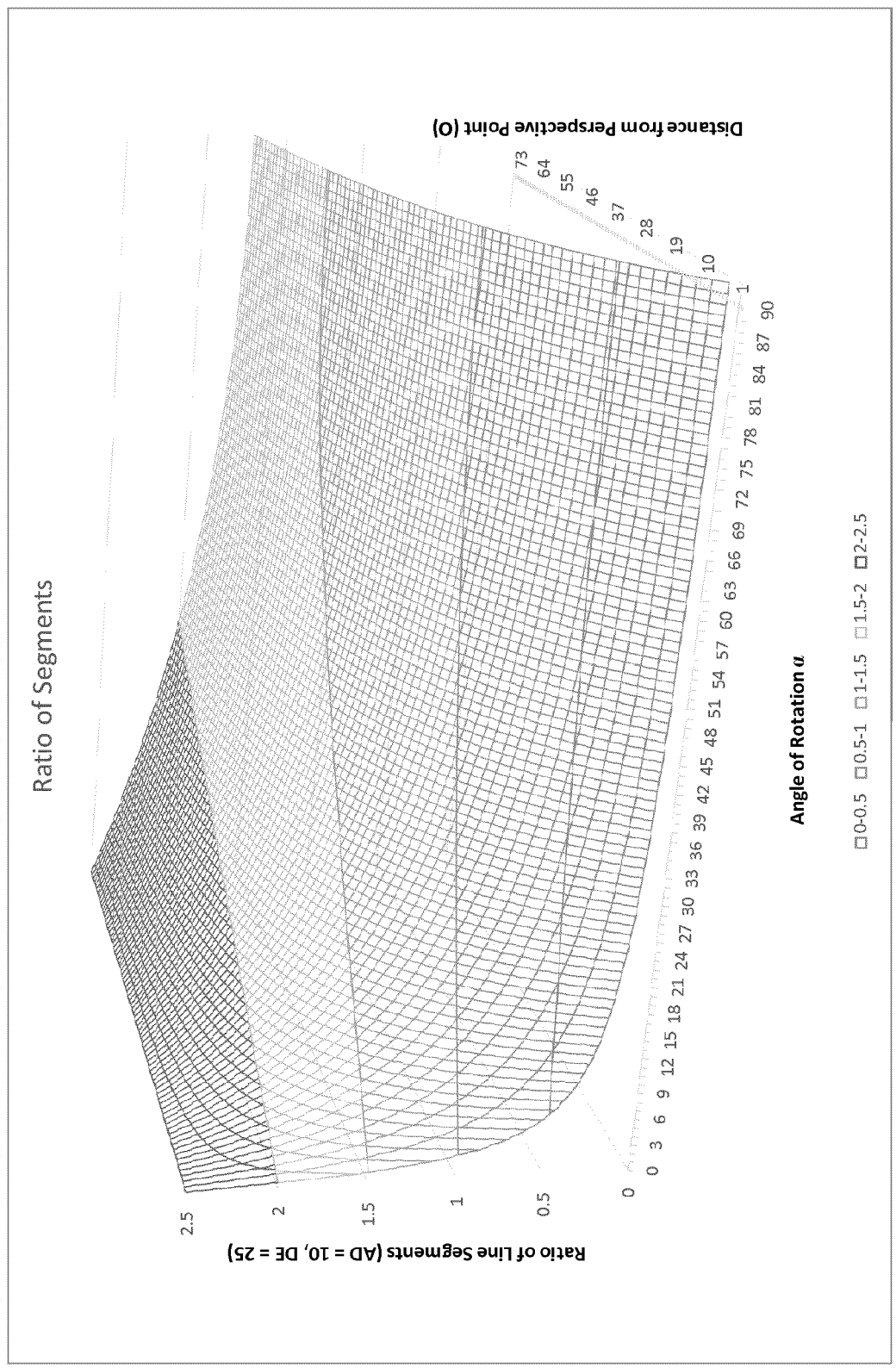
FIG. 12 illustrates the relationship between example line segments and their dependence on distance and angle of rotation.

This relationship is provided as follows:

$$\frac{B'C'}{A'B'} = \frac{DE*D2}{AD*[D2+(AD+DE)*\sin(\alpha)]} \quad (6)$$

Where the line segments AD and DE are the actual lengths of the line segments between the fiducials A and D and D and E respectively. These lengths may be chosen and optimized by design of the linear array of fiducials to maximize the variation in the ratios as in equation (6) above as described further below. The equation (6) contains two unknowns, specifically the angle $\alpha$ and the distance D2. FIG. 12 shows a plot of the relationship (6) above with independent variables $\alpha$ and D2, and the dependent variable as the ratio $$\frac{B'C'}{A'B'}.$$

It is apparent from the plot that each ratio value is unique in that the given function in the intervals defined by this plot is monotonic except for at 0° where the ratio of segments AD and DE are conserved independent of the linear array of fiducials' distance from the perspective point of the imaging detector (for reasons described above).

Given that the ratio $$\frac{B'C'}{A'B'}$$

can be determined from the captured image of the linear array of fiducials in a manner consistent with the pinhole camera model, this actual ratio can then be compared with the plot of theoretical ratios depicted in FIG. 12 to find the theoretical ratio value that is closest to the actual ratio's value. This can be accomplished using known computational methods, such as a nearest neighbor algorithm. Once the closest theoretical ratio value is found on the plot, its corresponding unique independent variable values of angle of rotation $\alpha'$ and distance D2' can be determined. These variable values may provide an acceptably close approximation to the angle of rotation α and the distance D2 of the actual linear array of fiducials, as depicted in the 2D pinhole camera model described above. The coarseness of the approximation may be selected based on the approximation algorithm, and may be selected based on the limit of the resolution of the imaging detector, for example.

Figure 13:
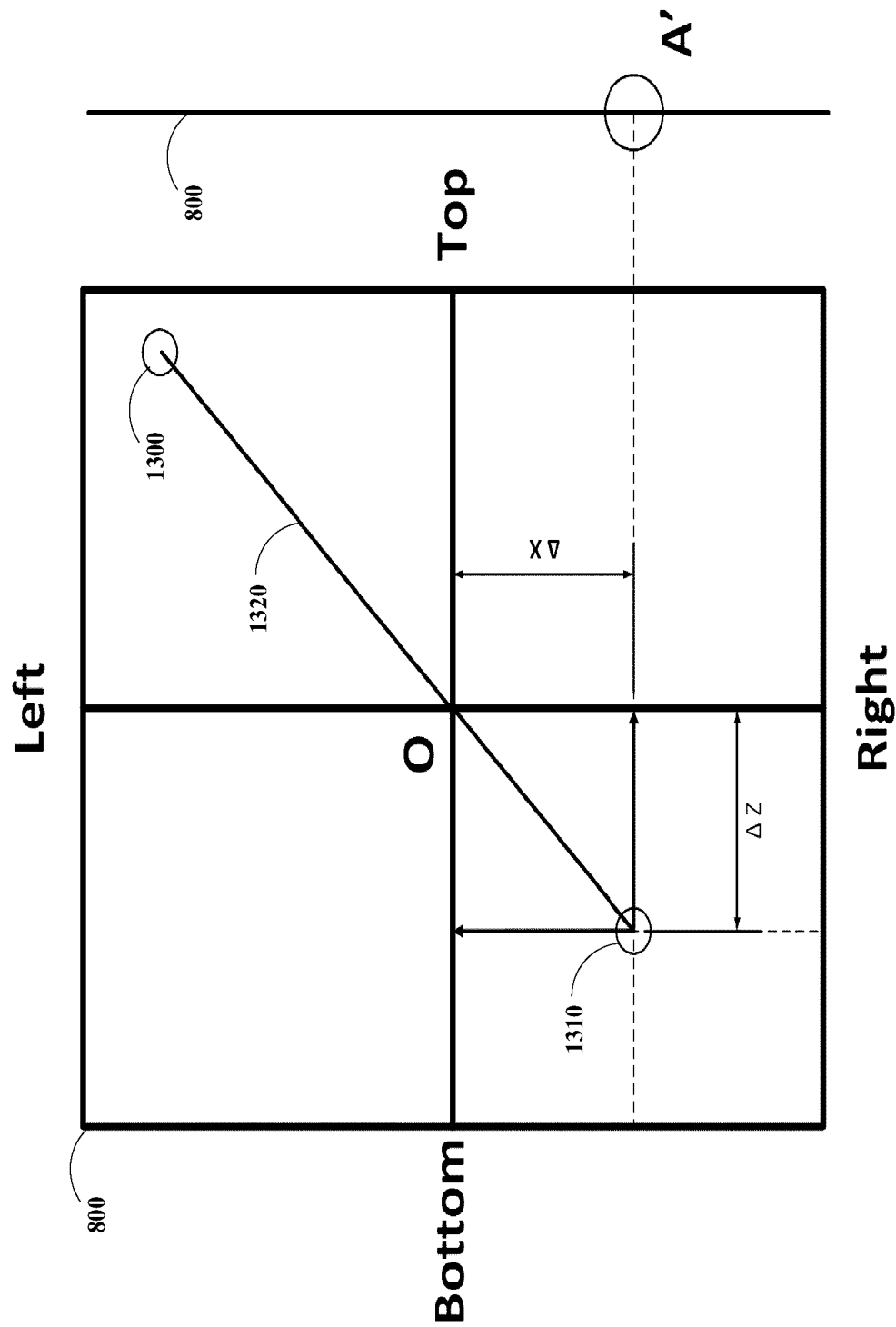
FIG. 13 illustrates an example 2D depiction of an image capture plane.

These variable values may then be used to calculate the estimated three-dimensional position and orientation (e.g., in six degrees of freedom, namely three angles of rotation and x, y, z coordinates; also referred to as the pose, location and depth) of the linear fiducial array with respect to the imaging detector as described below. FIG. 13 depicts the captured image containing the linear array of fiducials on the image plane 800 as follows from the 2D pinhole camera model. For simplicity, the figure does not show fiducials D and E and only fiducial A (shown as 1300), its projection line 1320 through the origin O onto the image plane 800, and its projected point A' (shown as 1310) are shown. The view in the figure is depicted facing outward from the imaging plane towards the imaged area from behind the plane. From this diagram it is apparent that the distances ΔX and ΔZ can be determined, where ΔX represents the distance of the projected point 1310 along the image plane 800 in the horizontal direction and ΔX represents the distance of the projected point 1310 along the image plane 800 in the vertical direction.

Figure 14:
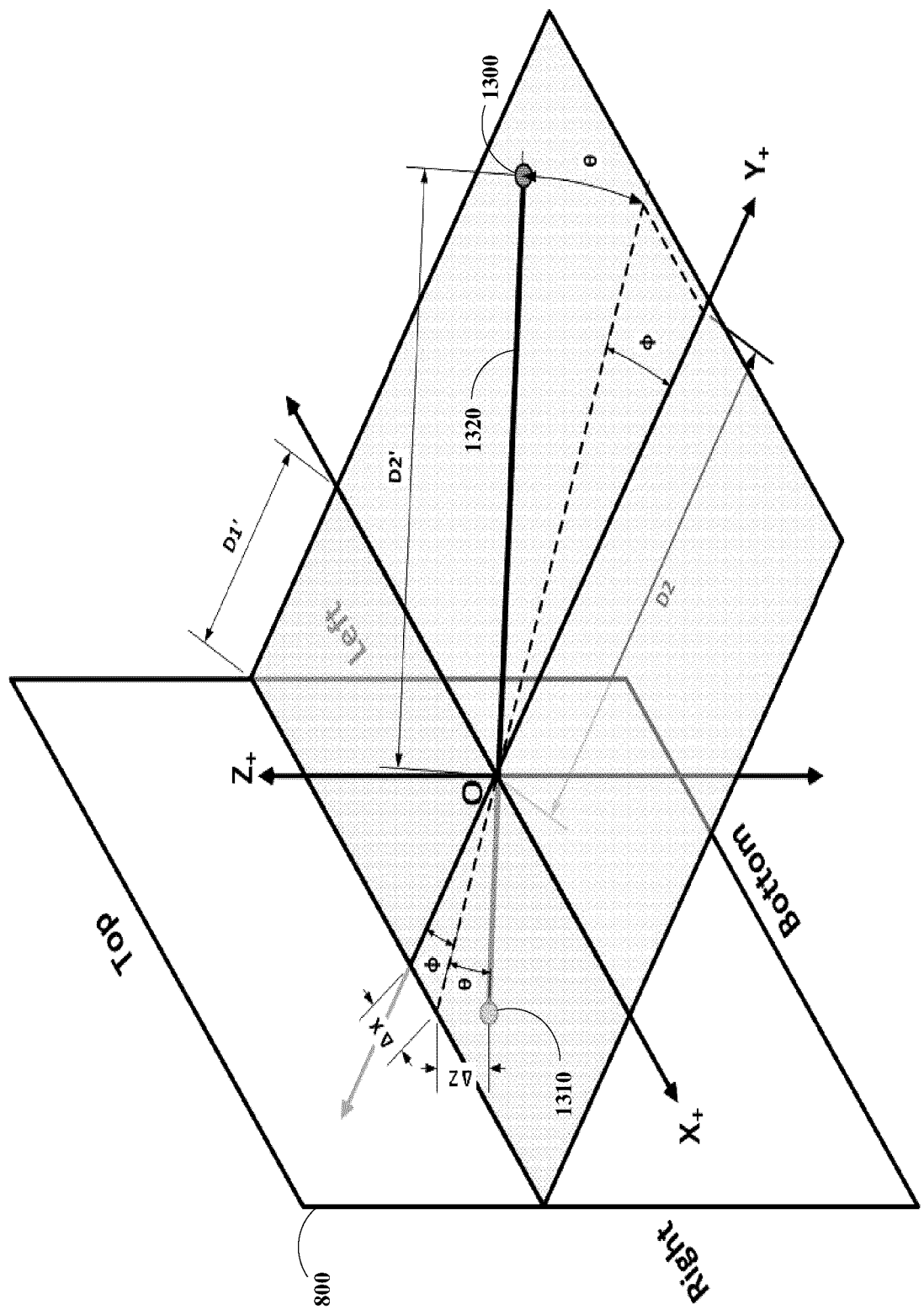
FIG. 14 illustrates an example 3D depiction of an image capture.

FIG. 14 depicts the diagram of FIG. 13 in a 3D perspective view, with added dimensions and coordinate axes centered at the Principle Point O. From this image, the exact location of point A (shown as 1300) can be calculated with respect to the principle point O located at the center of the image detector's sensor. This can be accomplished using spherical coordinates from the origin located at point O. The spherical coordinates will be defined as follows. The polar angle defined as the angle of rotation to the point on the XY plane relative to the defined 0° angle will be denoted φ, the azimuthal angle defined as the angle of rotation of the point from the XY plane towards the Z axis will be denoted θ, and the radius defined as the distance of the point from the origin will be denoted D2. It can be derived from the diagram in FIG. 14 using trigonometry that the projection line extending from point A (1300) to point A' (1310) will retain the same relative azimuthal φ and polar angle θ with the XY plane and the Y axis, respectively, on both sides of the ZX plane. This conservation of relative angles implicates that the distances associated with the projected point A' of fiducial A may be used to calculate the desired azimuthal φ and polar angles θ. Given the distances D1', ΔX, and ΔZ, the two angles and radius may be computed using the following equations:

$$\varphi = \tan^{-1}\left(\frac{\Delta X}{D1'}\right)$$

$$\theta = \tan^{-1}\left(\frac{\Delta Z}{\left(\frac{D1'}{\cos(\varphi)}\right)}\right)$$

$$D2' = \frac{D2}{\cos(\theta) * \cos(\varphi)}$$

The process described above can be repeated to determine the positions of points D and E as well, the only difference being the radius value will change depending on their projected distance from the origin on the Y axis. In FIG. 11 the distance D2 is the line segment OO" and the distance D2 is also the distance from the origin to the point A depicted by the line segment OA. For the points D and E these distances would change to the distances of line segments OO'" and OO"" and OD and OE, respectively. It then follows from FIG. 11 and the description above that the following equations would apply to calculating the radii of points D and E respectively.

$$OD = \frac{OO'''}{\cos(\theta) * \cos(\varphi)}$$

$$OE = \frac{OO''''}{\cos(\theta) * \cos(\varphi)}$$

These radii can then be used to determine the spherical coordinates of both points D and E with respect to the origin O. It should be noted that both points D and E will have varying azimuthal φ and polar angles θ depending on their projected points B' and C' locations in the imaging planes, respectively. Once spherical coordinates for all three points are acquired, the position of the linear array of fiducials and its orientation relative to the center of the imaging detector's sensor (i.e., the principle point O) will be known and may be used to track the linear array of fiducials. It should be noted that real time tracking may be done by performing the process above at a sufficiently high frequency (e.g., about or greater than 60 Hz, such as commonly used in LCD televisions).

Although one technique is described above, there may be other suitable methods for determining the 3D position and orientation of a line segment with mounted fiducials at known linear distances from one another, such as described in Computer and Robot Vision v.2 by Robert M. Haralick & Linda G Shapiro, Addison-Wesley Publishing Company, pp. 66-68, 1993, the entirely of which is hereby incorporated by reference. It should be noted that with the methods mentioned above, three or more fiducials may be used.

In some examples, a system for tracking a piece of medical equipment such as a medical instrument, in particular a surgical instrument, such as using the techniques discussed above, is disclosed. In the present disclosure, although reference is made to medical instruments and surgical instruments, it should be understood that other equipment may be tracked, including other medical equipment (e.g., an insertable image acquisition system) which may not necessarily be a medical instrument.

The system may include an array of active or passive fiducial markers, arranged collinearly as described above. Where the fiducial markers are active, each active fiducial marker may emit a signal, such as a light signal, at a respective unique frequency distinguishable from each other. Where the fiducial markers are passive, the passive fiducial markers may be arranged to define line segments of unique length, to enable disambiguation as discussed above. It should be noted that although active fiducial markers do not need to be arranged to define line segments of unique length (since active fiducial markers may be uniquely identified based on their respective unique emitted signals), active fiducial markers may also be arranged to define line segments of unique length. Such an arrangement may enable active fiducial markers to also operate as passive fiducial markers, for example. The fiducial markers may be arranged collinearly along the longitudinal axis of a medical instrument that is to be inserted through an access port, for example, towards a surgical site. The system may include a camera, such as a monocular camera, (e.g., surgical scope), for capturing static or live video images of the surgical site in a single image plane (generally referred to as a monocular camera for simplicity), including the medical instrument (and including the fiducial markers). The monocular camera may provide input to a processor, which may perform calculations to track the medical instrument, such as the calculations discussed above. The processor may segment representations of the fiducial markers from the captured image(s). For example, passive fiducial markers may be segmented from the capture image(s) using various suitable image processing techniques (e.g., techniques that detect and segment the reflective representations of the fiducial markers from a captured image). In the case of active fiducial markers, the segmenting may involve segmenting signals from the active fiducial markers from the captured image(s). For example, the processor may perform a frequency filtering or infrared filtering process to segment out the signals from the fiducial markers. The processor may then use these signals to calculate the orientation and position of the medical instrument, based on the known arrangement of the fiducial markers on the medical instrument. The processor may then determine the 3D orientation and position of the medical instrument relative to the monocular camera and/or register the orientation and position of the medical instrument within a virtual space, such as the image space of the image captured by the monocular camera or a 3D virtual space of an overall navigation system, as described below.

Where the system is part of an overall navigation system (e.g., as shown in FIG. 1B), the processor may, instead of or in addition to determining the 3D orientation and position of the medical instrument relative to the monocular camera, register the orientation and position of the medical instrument within a 3D virtual space defined by the navigation system. The navigation system may further enable tracking of passive markers (e.g., provided on the patient, provided on a reference location such as the patient's bed, provided on the access port and/or provided on other surgical instruments) within the virtual space, such as described in PCT application no. PCT/CA2014/050270 entitled "SYSTEMS AND METHODS FOR NAVIGATION AND SIMULATION OF INVASIVE THERAPY", previously incorporated by reference in its entirety.

In various practical applications of the present disclosure, design of the linear array of fiducials should be considered. Generally, for detection of the linear array of fiducials, a minimum separation length between adjacent fiducials should be defined, based on the minimal screen resolution at the maximum distance (from the surgical scope imaging sensor) where the linear array of fiducials may be required to operate at (i.e. when mounted on the surgical instrument). In addition, in order to determine the directionality of the surgical instrument when using identical fiducials (e.g., non-unique passive fiducial markers or active fiducial markers with non-unique emitted signals), the fiducials should be spaced such that when mirrored across a plane normal to and located at the center of the linear array of fiducials the mirrored fiducials are aligned differently than the fiducials located on the same side of the plane. Adhering to these constraints may help to assure that one side of the array may be differentiated from the other so the directionality of the surgical instrument can be determined. It should be noted that when using uniquely identifiable fiducials (e.g., active fiducials each having different signal frequencies) the constraint of having the fiducials positioned differently on both sides of the linear array of fiducials need not apply as one side can be identified by determining whether a specific identifiable fiducial is located on the distal or proximal side of the surgical instrument.

When using active fiducials such as flashing LEDs, modulated IR emitters, or other such active markers, the fiducials may be detected by methods such as described in the following papers: Lee, J., & Neumann, U. (n.d.). Rule-Based Segmentation for Intensity-Adaptive Fiducial Detection. Retrieved Aug. 20, 2014; Aitenbichler, E., & Muhlhauser, M. (2003). An IR Local Positioning System for Smart Items and Devices. IEEE; and Naimark, L., & Foxlin, E. (2005). Encoded LED System for Optical Trackers. IEEE, the entireties of which are hereby incorporated by reference. Possible advantages of using these active fiducials as opposed to their passive counterparts include, for example, their generally smaller size and reduced weight, and their inherent capacity to be uniquely coded to enable unique identification of each fiducial.

Figure 15:
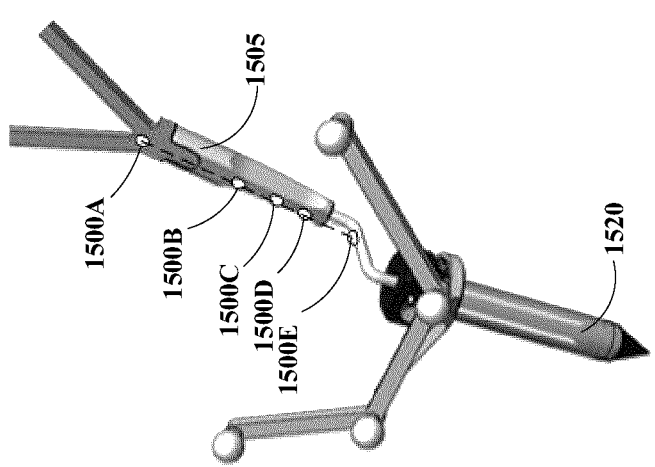
FIG. 15 illustrates an exemplary surgical tool mounted with a linear array of active fiducial markers.

FIG. 15 shows an exemplary medical instrument 1505 with a linear array of active fiducials formed by fiducials 1500A, 1500B, 1500C 1500D, and 1550E (in this example, active LEDs). The medical instrument 1505 may be inserted into the access port 1520, to access a surgical site. Chart 1510 describes different combinations of emitted signals (e.g., at different frequencies or wavelengths A-E in combination 1, F-J in combination 2, and K-O in combination 3) that can be used to code each fiducial, such that when tracking multiple instruments using the methods described above each fiducial can be uniquely identified. For example, when tracking two instruments having similar fiducials arranged in a similar linear array, the fiducials on the first instrument may emit signals according to combination 1 while the fiducials on the second instrument may emit signals according to combination 2. This may enable the processor to determine which set of fiducials belong with which medical instrument. In some examples, it may be possible to track two instruments having similar fiducials arranged in a similar linear array, without ambiguity, even when there is some overlap in the frequencies emitted by fiducials of the two instruments. For example, one instrument may have fiducials emitting signals at frequencies A-E while the second instrument may have fiducials emitting signals at frequencies E-I. It may still be possible to track these two instruments within ambiguity.

In addition, given the redundancy of fiducials (i.e. greater than the minimum number of three), if the bottom two fiducials (1500D and 1500E) become occluded by tissue or other obstructions in the surgical area of interest (e.g. occluded by portions of the access port 1520) then the other three fiducials 1500A, 1500B, 1500C can still be used to track the tool 1505. It should be noted that if the two most distal markers of any or all of the combinations shown in chart 1510 are occluded, each combination is still uniquely identifiable. This would not necessarily be the case with passive markers in that if the spatial coding of the markers is lost by occluding one of the distal redundant markers, then the tracking information may be rendered ambiguous, unusable, or inaccurate. Also, passive markers utilized commonly in surgery at present tend to be larger than the access permitted by most access corridors (e.g., access ports) and surgical openings used in minimally invasive surgeries, preventing the passive markers from being placed on any parts of the tool which is to be inserted into the patient via the surgical opening or which is operated in the corridor.

An arrangement which can be used to employ active fiducials but which avoids using active electronics directly on a tool may be accomplished through the use of fiber optics (in the case of light-emitting active fiducials) wherein each fiducial could include a light-transmitting fiber positioned to emit light at known locations along the length of a surgical instrument. In the example of FIG. 15, each of the fiducials 1500A-E may include a respective optical fiber which would travel through the tool 1505 to a light source (not shown), which may be separate from the tool 1505. In some examples, the light source may be located on the tool 1505, such as where the light source is sufficiently small and lightweight. Avoiding the placement of active electronics on the tool 1505 may help to reduce the size and/or weight of the tool 1505, and may also avoid any safety issues that may be associated with introducing active electronics into the surgical site, such as during intraoperative magnetic resonance imaging (MRI) procedures.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as ROM, volatile RAM, non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. A system for intraoperatively tracking at least one medical equipment within a three-dimensional virtual space in real time, the system comprising:
   at least one collinear array, each at least one collinear array comprising a plurality of fiducial markers, each fiducial marker disposed at a known fixed distance relative to another fiducial marker in relation to each at least one medical equipment, each plurality of fiducial markers distinct from another plurality of fiducial markers, and each plurality of fiducial markers comprising a distinct combination of fiducial markers;
   a camera for capturing an image of the at least one medical equipment on a single image plane, whereby a captured image is provided, the captured image comprising an image of at least some fiducial markers of the plurality of fiducial markers of each at least one medical equipment; and
   a processor receiving input from the camera and configured by a set of instructions to:
      segment a plurality of representations of the plurality of fiducial markers for each at least one medical equipment from the captured image, whereby a plurality of segmented representations are provided, the instruction to segment the plurality of representations comprising an instruction to filter at least one of frequency and wavelength;
      calculate a three-dimensional orientation and a position of each at least one medical equipment using the plurality of segmented representations;
      track the three-dimensional orientation and the position of each at least one medical equipment relative to the camera; and
      register the three-dimensional orientation and the position of each at least one medical equipment within the three-dimensional virtual space, wherein the plurality of fiducial markers comprises a plurality of active fiducial markers configured to emit a plurality of signals, each active fiducial marker of the plurality of active fiducial markers configured to emit a signal at a distinct frequency relative to another active fiducial marker, each active fiducial marker comprising a light-emitting optical fiber and a flashing light-emitting diode, the flashing light-emitting diode coupled with the light-emitting optical fiber, the distinct combination of fiducial markers comprising a distinct combination of frequencies to uniquely identify each at each at least one medical equipment, and the distinct frequency comprising a frequency range of at least 60 Hz to achieve real-time tracking of the plurality of fiducial markers, whereby each at least one medical equipment is trackable in real time, and whereby each at least one medical equipment is distinguishable from another at least one medical equipment.

2. The system of claim 1, wherein the plurality of fiducial markers further comprises a plurality of passive fiducial markers, wherein the known fixed distance is unique, and wherein each active fiducial marker further comprises a modulated infrared emitter.

3. The system of claim 1, wherein the processor is configured to segment the plurality of representations by segmenting the plurality of signals emitted by the plurality of active fiducial markers from the captured image.

4. The system of claim 3, wherein the known fixed distance is unique.

5. The system of claim 1, wherein the plurality of fiducial markers is collinearly disposed along a longitudinal axis of the medical equipment.

6. The system of claim 1, wherein the camera comprises a monocular camera.

7. The system of claim 1, wherein the camera comprises a video camera.

8. The system of claim 1, wherein the medical equipment comprises a surgical instrument.

9. A surgical navigation system for intraoperatively tracking at least one medical equipment in real time, the system comprising:

a first medical equipment;

a first collinear array comprising a plurality of a first set of fiducial markers coupled with a first medical equipment of the at least one medical equipment, each fiducial marker of the first set of fiducial markers disposed at a known fixed distance relative to another fiducial marker of the first set of fiducial markers in relation to the first medical equipment, each fiducial marker distinct from another fiducial marker of the first set of fiducial markers;

a first camera for capturing an image of the first medical equipment on a single image plane, whereby a captured image is provided, the captured image comprising an image of at least some fiducial markers of the first set of fiducial markers;

a second camera for tracking a second set of fiducial markers; and a processor receiving input from the first camera and the second camera, the processor configured by a set of instructions to:

register the second set of fiducial markers within a three-dimensional virtual space;

segment a plurality of representations of the first set of fiducial markers from the captured image, whereby a plurality of segmented representations is provided;

calculate a three-dimensional orientation and a position of the first medical equipment using the plurality of segmented representations; and register the three-dimensional orientation and the position of the first medical equipment within the three-dimensional virtual space, wherein the first set of fiducial markers comprises a plurality of active fiducial markers configured to emit a plurality of signals, each active fiducial marker of the plurality of active fiducial markers configured to emit a signal at a distinct frequency relative to another active fiducial marker, and each active fiducial marker comprising at least one light-emitting optical fiber and a flashing light-emitting diode, the flashing light-emitting diode coupled with the light-emitting optical fiber, the first set of fiducial markers comprising a combination of fiducial markers distinct in relation to the second set of fiducial markers, the distinct combination of the first set of fiducial markers comprising a distinct combination of frequencies to uniquely identify the first medical equipment, and the distinct frequency comprising a frequency range of at least 60 Hz to achieve real-time tracking of the plurality of fiducial markers, whereby each at least one medical equipment is trackable in real time, and whereby each at least one medical equipment is distinguishable from another at least one medical equipment.

10. The system of claim 9, further comprising a second medical equipment having the second set of fiducial markers coupled thereto, the second set of fiducial markers comprising a plurality of passive fiducial markers, wherein each active fiducial marker further comprises a modulated infrared emitter.

11. The system of claim 10, wherein the second medical equipment comprises an access port providing an access corridor for accessing a surgical site, and wherein the first medical equipment comprises a surgical instrument that is at least partially insertable into the access corridor.

12. The system of claim 9, wherein the first medical equipment comprises a surgical instrument.

13. The system of claim 9, wherein the first set of fiducial markers comprises a plurality of passive fiducial markers, and wherein the known fixed distance is unique.

14. The system of claim 9, wherein segmenting the plurality of representations comprise segmenting the plurality of signals emitted by the first set of fiducial markers from the captured image.

15. The system of claim 14 wherein the known fixed distance is unique.

16. The system of claim 9, wherein the first set of fiducial markers are-collinearly disposed along a longitudinal axis of the first medical equipment.

17. The system of claim 9, wherein the first camera comprises a monocular camera, and wherein the second camera comprises a binocular camera.

18. The system of claim 9, wherein the first camera comprises a video camera.

19. The system of claim 9, wherein the second camera comprises a stereoscopic camera.

20. A method of fabricating a system for intraoperatively tracking at least one medical equipment within a three-dimensional virtual space in real time, the method comprising:

providing at least one collinear array, each at least one collinear array comprising a plurality of fiducial markers, each fiducial marker disposed at a known fixed distance relative to another fiducial marker in relation to each at least one medical equipment, each plurality of fiducial markers distinct from another plurality of fiducial markers, and each plurality of fiducial markers comprising a distinct combination of fiducial markers;

providing a camera for capturing an image of the at least one medical equipment on a single image plane, whereby a captured image is provided, the captured image comprising an image of at least some fiducial markers of the plurality of fiducial markers of each at least one medical equipment; and providing a processor configured to receive input from the camera and configured by a set of instructions to:

segment a plurality of representations of the plurality of fiducial markers for each at least one medical equipment from the captured image, whereby a plurality of segmented representations are provided, the instruction to segment the plurality of representations comprising an instruction to filter at least one of frequency and wavelength;

calculate a three-dimensional orientation and a position of each at least one medical equipment using the plurality of segmented representations;

track the three-dimensional orientation and the position of each at least one medical equipment relative to the camera; and register the three-dimensional orientation and the position of each at least one medical equipment within the three-dimensional virtual space, wherein the plurality of fiducial markers comprises a plurality of active fiducial markers configured to emit a plurality of signals, each active fiducial marker of the plurality of active fiducial markers configured to emit a signal at a distinct frequency relative to another active fiducial marker, each active fiducial marker comprising a light-emitting optical fiber and a flashing light-emitting diode, the flashing light-emitting diode coupled with the light-emitting optical fiber, the distinct combination of fiducial markers comprising a distinct combination of frequencies to uniquely identify each at each at least one medical equipment, and the distinct frequency comprising a frequency range of at least 60 Hz to achieve real-time tracking of the plurality of fiducial markers, whereby each at least one medical equipment is trackable in real time, and whereby each at least one medical equipment is distinguishable from another at least one medical equipment.

* * * * *